United States Patent [19]
Jensen

[11] 4,116,074
[45] Sep. 26, 1978

[54] METHOD AND APPARATUS FOR THE EXAMINATION OF BODIES

[76] Inventor: Palle Rasmus Jensen, Forhabningsholms Alle 30; 1904, Copenhagen V, Denmark

[21] Appl. No.: 721,958

[22] Filed: Sep. 10, 1976

[30] Foreign Application Priority Data

Sep. 12, 1975 [DK] Denmark .................. 4079/75

[51] Int. Cl.² ............................................. G01N 29/00
[52] U.S. Cl. ........................................ 73/607; 73/620; 128/2 V
[58] Field of Search ............. 73/67.7, 67.5 R, 67.8 R, 73/67.8 S, 67.9, 607, 620, 627, 629; 128/2 V

[56] References Cited

U.S. PATENT DOCUMENTS

| | | | |
|---|---|---|---|
| 3,461,420 | 8/1969 | Silverman | 73/67.7 |
| 3,543,229 | 11/1970 | Baum | 73/67.8 S |
| 3,688,564 | 9/1972 | McDicken | 73/67.8 S |
| 3,780,572 | 12/1973 | Rocha | 73/67.7 |
| 3,962,909 | 6/1976 | Lund | 73/67.8 S |
| 3,964,297 | 6/1976 | Jorgensen et al. | 73/67.9 |

*Primary Examiner*—Richard C. Queisser
*Assistant Examiner*—Stephen A. Kreitman
*Attorney, Agent, or Firm*—Kenyon & Kenyon

[57] ABSTRACT

A method and apparatus for facilitating examination of an object within an optically opaque body through the use of impulse-echo techniques by projecting to an observation point, via a reflective surface positioned to intersect a line between the observation point and the object to be examined, a virtual image of a linear array of luminous points corresponding to echo-producing points of the object, such that each luminous point of the reflected image appears at a location, relative to the observation point, that coincides with the actual location of the corresponding echo-producing point of the object in the body.

21 Claims, 10 Drawing Figures

METHOD AND APPARATUS FOR THE EXAMINATION OF BODIES

BACKGROUND OF THE INVENTION

The invention relates in particular to the scanning technique based on ultra-sound according to the impulse-echo principle. This technique is generally performed in one of two possible manners.

The first is the use of the socalled B-scanning, which normally implies the scanning of a sectional plane through the object and a running registration of the positions of reflecting structures in the said sectional plane. The result is that after a few minutes of scanning it will be possible to have drawn up a two-dimensional picture on a storage-oscilloscope, showing the intersections of the reflecting structures with the sectional plane.

The second is the use of socalled dynamic scanning, which implies a rapid scanning of a limited area permitting utilization of the short-time memorizing of the eye for the formation of a picture.

B-scanning by way of a storage-oscilloscope represents the most widely used procedure, but it has a major drawback in that it takes a long time to draw up a satisfactory picture. It is accordingly required to form the entire picture before it is possible to see whether it is satisfactory, and then to wipe it off again entirely to adjust amplification etc.m before the next picture is registered. In the meantime, however, the conditions to be examined may have changed.

This may, for instance, be the case, if we are dealing with a fetus, which is moving. If we examine parts of the human body we have moreover no clear impression of the relation of the sectional picture to the body, as picture and body are placed at some distance from each other.

Dynamic scanning represents a more recent method, which in certain relations offers improvement in comparison with the B-scanning. Due to the rapid, automatically repeated scanning it is easier to make adjustments to obtain a better picture, as it will be possible to detect alterations instantly. Nor will there be any problems with regard to alterations of the conditions of the examined object, as it will be possible to ascertain such alterations directly during the scanning.

In spite of these improvements of the manner of producing the scanning pictures, there will still remain two problems unsolved:

1. You will only get a picture answering the section of the body being examined, which will complicate the formation of a picture of the entire spatial form and extent of a given structure.
2. You will have no direct idea of the position of the the examined body reproduced. Alterations of the scanning angle and position will bring about a change of the picture, but due to the appearance of the picture on a stationary screen, no particularly good impression of the position of a depicted structures is left.

SUMMARY OF THE INVENTION

It is the object of the invention to remedy these two disadvantages, and the method is characterized in that the indications by means of an arrangement of one or more mirrors is shown as imaginary luminous points placed preferably in exactly the position in an object, where a reflecting structure is actually found.

In this way the latter drawback has been overcome. The said method can be realized in many different ways by means of one or several mirrors, and it has proved possible by way of several of the possible embodiments to overcome the former drawback as well.

The invention relates likewise to an apparatus for the performance of the method, which said apparatus is provided with a transmitter for e.g. ultrasound or radar, made to emit impulses out along the first line and to receive the reflected echos along the same line, and to indicate the reflections as luminous points along the second line. The said apparatus is characterized by having between the two lines reflecting media for the formation of the imaginary picture. By the use of such media it is possible in a simple manner to form the desired picture, although it might even be imagined that the picture was formed for instance by way of optical and electronic devices.

An advantageous embodiment of the said apparatus is characteristic by providing devices for forward and backward swinging in one plane of the first line i.e. the line along which the impulses are emitted and the reflections received, and by having devices for the swinging of the second line either direct or in the form of a mirror image synchronous with the former. Thus in an uncomplicated manner, an idea of the echo-producing structures situated in a definite section is rendered and be it noticed to have the said section placed as an imaginary picture in a correct way in relation to the object being examined. By moving the apparatus sideways in relation to the plane in which the swinging takes place it will be simple to scan for a certain echo-producing structure in the object under examination.

A further embodiment is characteristic in that it has a stationary film camera in the room intended for long-time exposures. By likewise having the examined object stationarily placed in the room it will thus be possible to scan a certain area of the object and hereby attain a summing up in the film camera of the generated indications. It should in this connection be pointed out that it is relatively immaterial how the apparatus is moved within the searched area, as the said picture will appear distinct if only the requirement that camera and object area stationarily placed during the exposure is complied with.

A particularly advantageous embodiment of the apparatus concerned is characteristic in that it is made for the filming of three-dimensional pictures by way of stereo-technique. This leaves the possibility by studying the resultant three-dimensional picture to have a spatial impression of the echo-producing structures in position to each other, which means an impression of the distances between the echo-producing structures within the object.

Another similar embodiment is characteristic by having a stationary television camera stationarily placed in the room coupled with a storage oscilloscope in such a manner that the pictorial information is summed up. This offers principally the same advantage as the use of a stationary film camera but moreover a further advantage permitting a rapid wiping off of the appeared picture and allowing the study of the picture during the formation. Another embodiment of the latter apparatus can in a like manner be characteristic in that the camera is intended for the filming of three-dimensional pictures by way of stereo-technique. Hereby is achieved an entirely special effect allowing the study of the spatial picture during its formation and hence to conduct the transducer to the place where it must be relevant to have produced the spatial structure of special interest.

The apparatus may further be characterized by a programme-guided unit, devised for production of an even scanning pattern. Production of an even scanning pattern is of importance to the quality of the picture, just as it is important to a photograph to secure a uniform exposure of the individual sectors of the picture to reproduce a correct impression of the contrasts in the picture.

The embodiment of the apparatus described above can be characterized in that the devices for the production of the swings are made to swing at a frequency sufficient high for retaining the impression of light on the retina of the human eye, as the apparatus is constructed for work with impulse repetition frequencies considerably higher than the swinging frequency. It is in this way possible in a more safe manner to obtain an impression of the positions of the echo-producing structures in a certain section, as the entire section may constantly be studied in the form of constant luminous points in the place where the echo-producing structure remains.

Another embodiment for the achievement of the same effect is characteristic in having media for plotting of the indications of the second line on a storage display e.g. in the form of a LCD-display (liquid crystals), a storage oscilloscope or on magnetic paper, and having possibilities for preservation of the said indications on the display for a period equal to at least the time passing between two successive swings. By way of the mentioned embodiment it is possible to perform the said swingings at a lower frequency than the one required for the maintenance of impressions of light on the retina of the human eye, whereby it is avoided to strain the swinging mechanical parts so much.

A third embodiment for the attainment of the same optical impression as far as the study of the individual section concerns, is characterized by the means for swinging of the first line at a certain initial frequency, means for reading of the received echoes with corresponding distances in a buffer-memory, means for swinging of the second line at a certain second frequency higher than the former and sufficiently high to retain the impressions of light on the retina of the human eye, and means for repeated transmission of the indications of light from the buffer-memory to a series of light indicators along the second line synchronous with the movement of the latter.

This may bring about the further advantage of sparing mechanical parts which would otherwise swing at higher frequency.

An over-all general embodiment applicable in connection with all other embodiments of the apparatus consisting in a support of transmitter, receiver and mirror arrangement is characterized in that the support is mounted on a connecting rod mounted longitudinally displaceable in a stationary cardan suspension. Some of the weight of these parts is thus in a simple manner transferred to the firm support, which makes it easier to handle the apparatus in connection with the examination for example of a person. It is furthermore achieved that the mirror will always remain in a convenient position relative to the memorizing of the picture (camera or eye).

An apparatus of the said description, provided with a holder for a number of lamps or light indicators may further be characterized by the arrangements shown in FIGS. 8 and 9. Thus it is avoided to perform a swinging of the said light indicators with the appertaining wires, which represent a noticeable mass compared to the mirror, which is now instead swinging forwards and backwards at a frequency equal to at least 16 oscillations per second. The reduction of the swinging mass will, at the same time, mean, that the apparatus as such will only offer insignificant shaking. It has moreover proved more agreeable to look down into a stationary mirror.

An embodiment of the apparatus provided with a holder for a number of lamps or light indicators can be characterized by a first mirror, a transducer, made to swing round a first axis, a second axis, parallel with the first axis, and which in relation to the first axis is placed symmetrically round the plane of the first mirror, an indicator row, made to swing round the other axis in such a manner that the reflected picture in the other mirror, passing through the second axis, is situated symmetrically with the first line round the plane of the first mirror, as the reflecting faces of the mirrors are turned against each other.

The result is a very compact construction, and the swinging parts will be made to swing in opposition, whereby they will outbalance each other to a certain degree.

BRIEF DESCRIPTION OF THE DRAWINGS

The invention is described in detail below with reference to the drawing in which.

DESCRIPTION OF THE PREFERRED EMBODIMENTS

Figure 1:
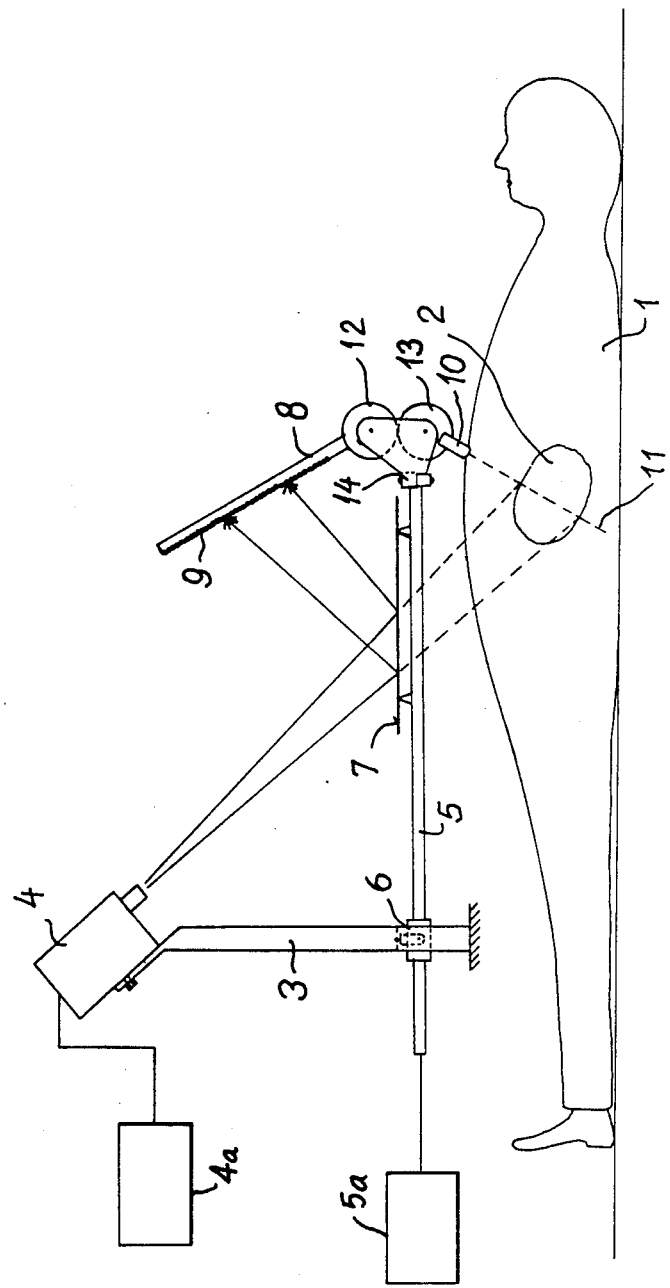
FIG. 1 shows an embodiment of an apparatus according to the invention, viewed schematically from one side, and in which the apparatus is applied for examination of a person lying on his back.

FIG. 1 shows a lying person 1, viewed from one side, having an inner organ 2, which is to be examined by means of ultra-sound. A stationary arrangement 3 serves as support for a stereo camera 4, which may be a film camera or a television camera, and for a connecting rod 5 mounted longitudinally displaceable in a cardan suspension 6 of the support 3. On the connecting rod 5 is mounted a mirror 7, the reflecting surface of which is turning upwards. At the end of the rod 5 is mounted a pivot-hung holder 8 for a number of lamps or light-diodes 9. The holder 8 is designed to swing in a plane perpendicularly on the plane of the mirror 7, and which may possibly pass through the connecting rod 5. On the opposite side of the plane of the mirror 7 is, in a similar manner suspended, a pivot-hung transmitter and receiver 10 for ultra-sound made for the transmission and reception of ultra-sound along a line 11, pivoting symmetrically with the row of lamps 9 round the plane of the mirror 7. The transmitter 10 and the holder 8 are each mounted on gears or toothed rims 12 and 13 in mesh. The transmitter 10 and the row of lamps 9 are moreover mutually connected by means of known electronic means (not shown) in such a manner that the row of echoes along the line 11 are reproduced along the row of lamps 9 in such a way that at any time lighted lamps are placed symmetrically with respect to the corresponding echo producing structure around the plane of the mirror. Thus, as seen from the camera 4 in the mirror, will appear a non-inverted mirror-image of the echoes of the positions, from where they appear. In the rod 5 there is between the mirror 7 and the holder 8 or the transmitter 10, a built-in charnier 14 with an axis perpendicularly on the plane of the mirror 7.

The apparatus will now function in the following way: When the rod 5 with the mounted parts is moved forwards and backwards or sideways, there will be seen in the mirror 7, from the stationary position of the camera 4, gleams from the inner organ 2 precisely corresponding to points, which are echo-producing. This will also be the case, if the scanning takes place by way of a swinging of the holder 8 and the transmitter 10 towards each other or apart from each other and probably also round the charnier 14. By reproducing all the echoes during a three-dimensional scanning on, for instance, the same photographic plate in a stereo-camera, that is leaving the shutter of the camera open during the entire scanning process, it will be possible to produce a three-dimensional picture of the echo-producing structures in the inner organ. The only condition is that the inner organ 2 and the camera 4 remains in a fixed position mutually during the scanning. Instead of a photographic camera, a television camera with a pictorial memory and a viewer may advantageously be used. In this way it is possible, during the scanning process, to guide it in such a manner that the desired pictures are produced. It is moreover possible at any time to wipe off the received signals and start afresh.

Similarly, other information storage devices 4a may be used as a means to record the reflected images and to develop a pictorial view of the ultrasonic echoes. The storage device 4a could be a LCD - display (liquid crystals), a storage oscilloscope or a magnetic paper. The storage device 4a would have the capability of preserving the reflected image of the display of luminous points for a period equal to at least the time passing between two successive swings. Through the use of such a storage device, it allows the holder 8 to swing at a frequency below what would be required to retain an image on the human retina and, therefore, avoid unnecessary mechanical strain on the apparatus.

The apparatus may be further provided with a program-guided unit 5a which will insure an even scanning pattern. Even scanning is important to insure that a high quality picture is attained. Uneven scanning would result in point exposures on a photographic film or television camera which would not properly correspond to the actual echo produced.

An other method to determine where and how the pictures shall be taken is to study the picture with the human eye simultaneously with the rapid scanning movements.

Figure 2:
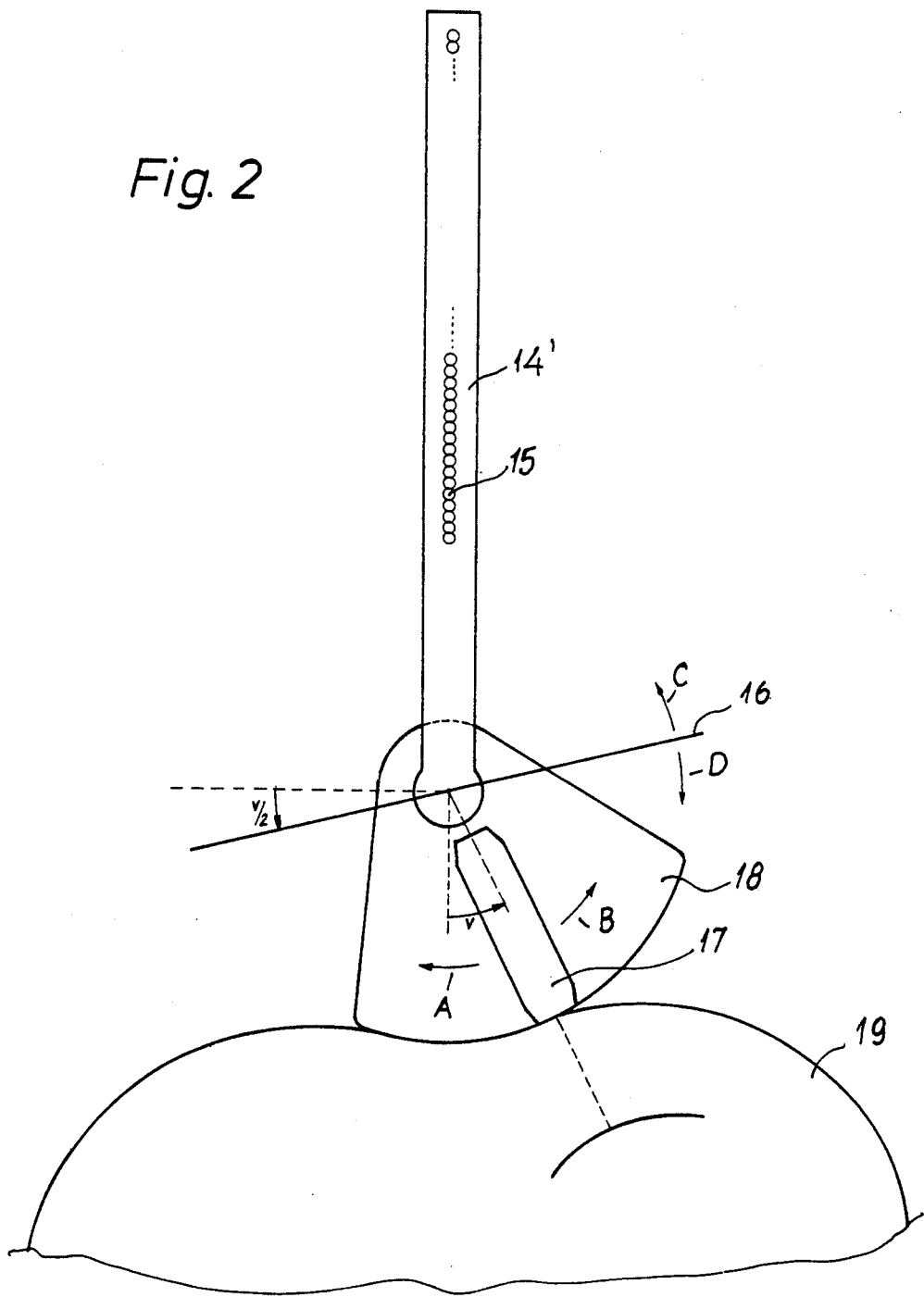
FIG. 2 shows another embodiment of the apparatus according to the invention, viewed schematically from the end, and in which the apparatus is applied for scanning in a soft body.

FIG. 2 shows schematically another embodiment of an apparatus according to the invention. A holder 14 for a number of lamps 15 is coupled pivotably to a mirror 16 and to a transmitter and receiver 17 for ultra-sound, which is mounted on a plate 18 formed like a circle segment. A (not shown) motor is designed for bringing this plate 18 with the transmitter 17 in an oscillating movement as shown by the arrows A and B, simultaneously as the mirror 16 is exposed to a similar movement as shown by the arrows C and D, but all the time with an angular deflection half as great. In this manner a scanning of a body 19 can be performed within the angle determined by the swinging movement of the transmitter 17. The latter embodiment is distinguished by a simple construction, as it is possible to to hold the apparatus manually in the holder 14, while the remaining parts are moving. The lamps 15 are thus stationary, while in the swinging mirror is reflected a correctly situated picture provided the oscillating movement is of a frequency equal to at least 16 fields (oscillations) per second.

Figure 3:
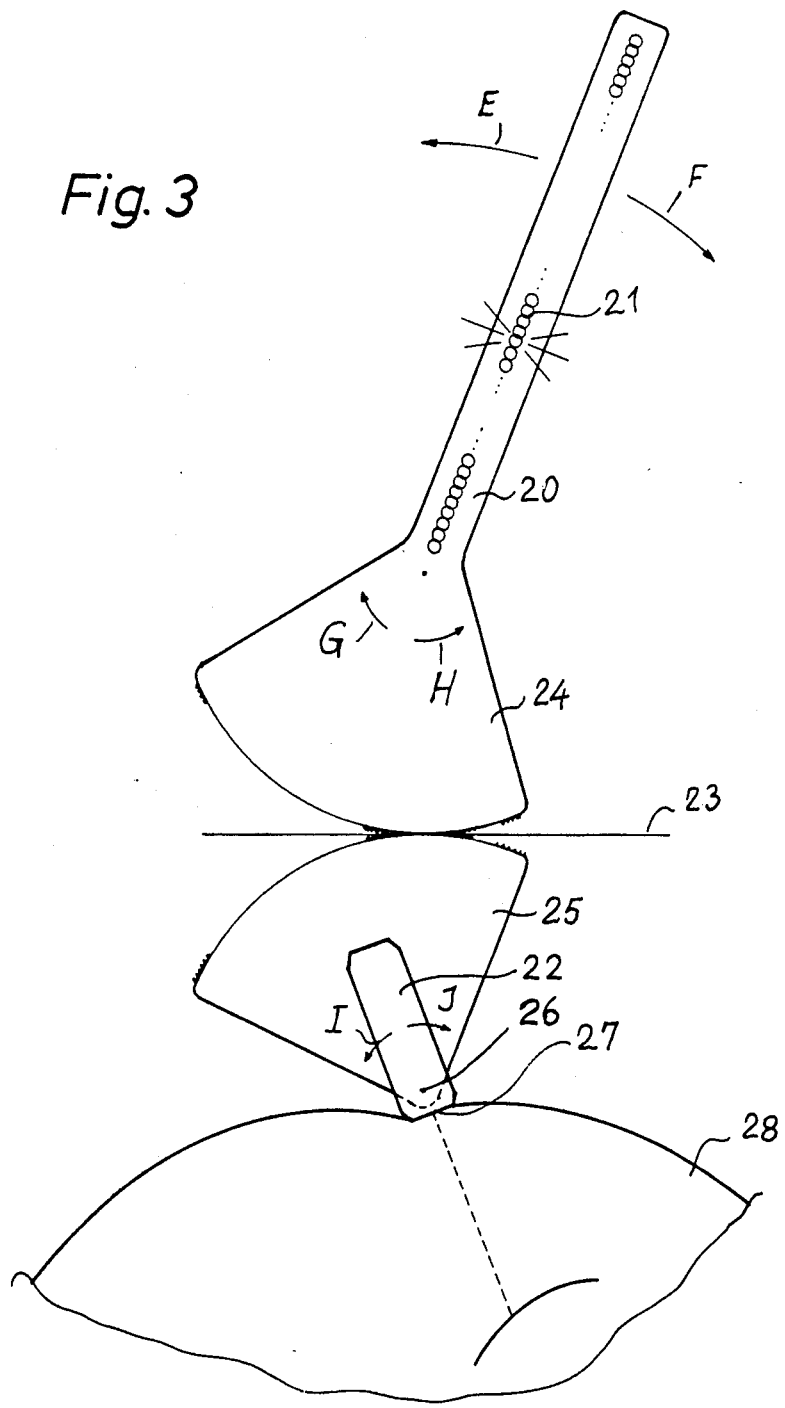
FIG. 3 shows a third embodiment of the apparatus.

FIG. 3 shows likewise schematically an apparatus for ultra-sound examinations. This apparatus is constructed to perform a synchronously oscillating movement of a holder 20 for a row of lamps 21 and a transmitter 22, as shown by the arrows E and F, G and H, I or J, whereas a mirror 23 is fixed in relation to the swinging parts mentioned. The synchronous movement is produced by mounting the holder 20 and the transmitter 22 each on a cogged link, 24 and 25 respectively. By this construction the centre of rotation 26 will come close to the contact point 27 required for examinations with ultra-sound of a firm, or deformable body 28, for instance the body of an animal. Thus a good contact is attained. The swinging holder 20 with the lamps 21 lighting at different times will produce a laterally reversed picture when viewed direct. If on the other hand the picture is seen in the mirror the result will be a non-inverted correctly situated picture.

Figure 4:
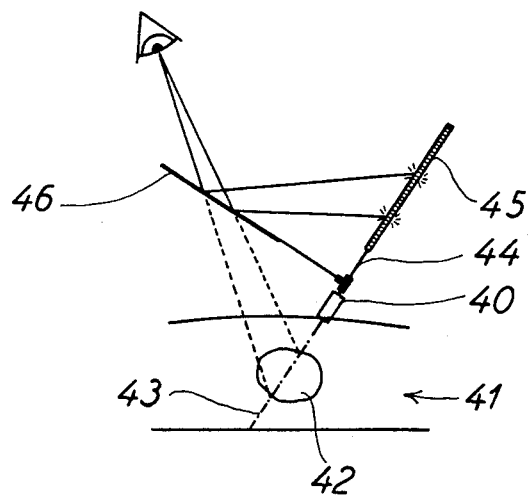
FIG. 4 shows an arrangement of mirrors, viewed from one side, of an apparatus according to a fourth embodiment.

FIG. 4 shows schematically a transducer 40 bearing against a body 41 containing an echo-producing structure 42. The first line 43 along which the impulses are emitted is placed end to end with the second line 44, along which are placed indicator lamps 45. Perpendicularly on the said joint line (43,44) is placed a mirror 46 with upward-turned reflecting face. The indicator lamps 45 are now mutually situated in such a manner that an echo from a given point will produce an imaginary luminous spot on the very place, when seen down in the mirror as indicated by the shown sight lines.

Figure 5:
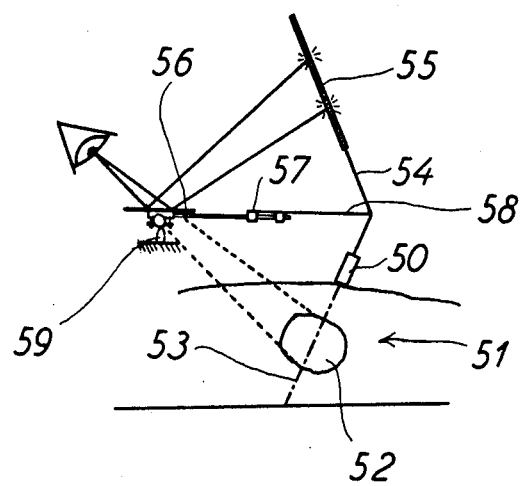
FIG. 5 shows an arrangement of mirrors, viewed from the side according to a fifth embodiment.

FIG. 5 shows schematically a transducer 50 bearing against a body 51 containing an echo-producing structure 52. The first line 53, along which the impulses are emitted is crossing the second line 54, along which the indicator lamps 55 are placed. A mirror 56 is placed in the plane of symmetry of the two lines, as, however, the distance from the mirror to respectively transducer 50 and indicator lamps 55 may be varied through a displacement link 57 of a connecting rod 58, for instance through a swinging forward/backward translatory movement. The mirror 56 is moreover fixed at a certain distance from a firm point 59. If this distance is small we can be certain that the examined part of the body 51 can be covered by the mirror most of the time.

Figure 6:
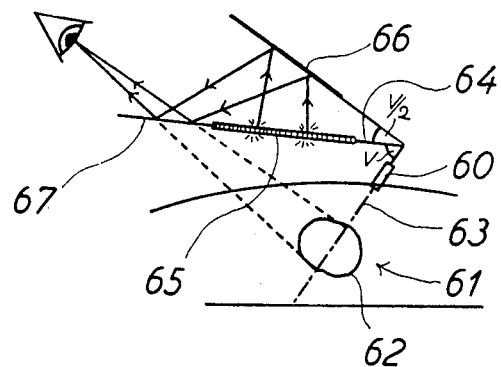
FIG. 6 shows a sixth embodiment of the invention from a side view.

FIG. 6 shows schematically a transducer 60 bearing against a body 61 containing an echo-producing structure 62. The first line 63, along which the impulses are emitted, forms an angle $v + \frac{1}{2}v = 1\frac{1}{2}v$ to a plane mirror 66 with a downward-turned reflecting face. The second line 64, along which the indicator lamps 65 are placed, is situated in a plane (plane of the paper) perpendicular on the plane of the mirror 66 containing the first line 63. The second line 64 forms at the same time an angle $\frac{1}{2}v$ to the plane of the said mirror in the plane of the paper. Another mirror 67 having an upward-turned reflecting face is eventually placed perpendicularly on the plane of the paper and contains the second line 64. By adapting the indicator lamps in a suitable way it is now possible to attain a radiation pattern, as shown, which gives a highly compact construction of the apparatus.

Figure 7:
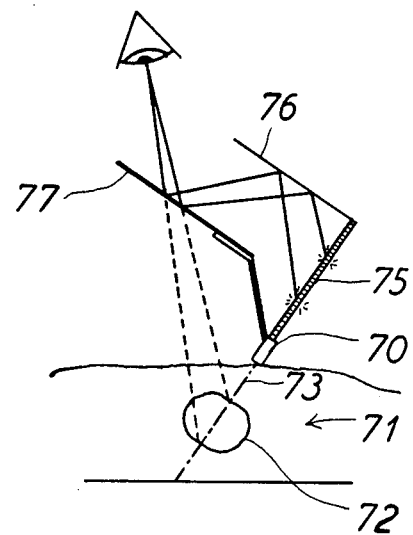
FIG. 7 shows a seventh embodiment of the invention from a side view.

FIG. 7 shows a transducer 70 bearing against a body 71 containing an echo-producing structure 72. The first line 73, along which the impulses are emitted, is placed end to end with the second line, along which the indicator lamps 75 are situated. Perpendicularly on the line 73 are placed mirrors 76 and 77 with the reflecting surfaces facing each other.

By adapting the indicator lamps and the mirrors in a suitable way it is possible to attain a radiation pattern as shown, and a compact construction will be the result.

Figure 8:
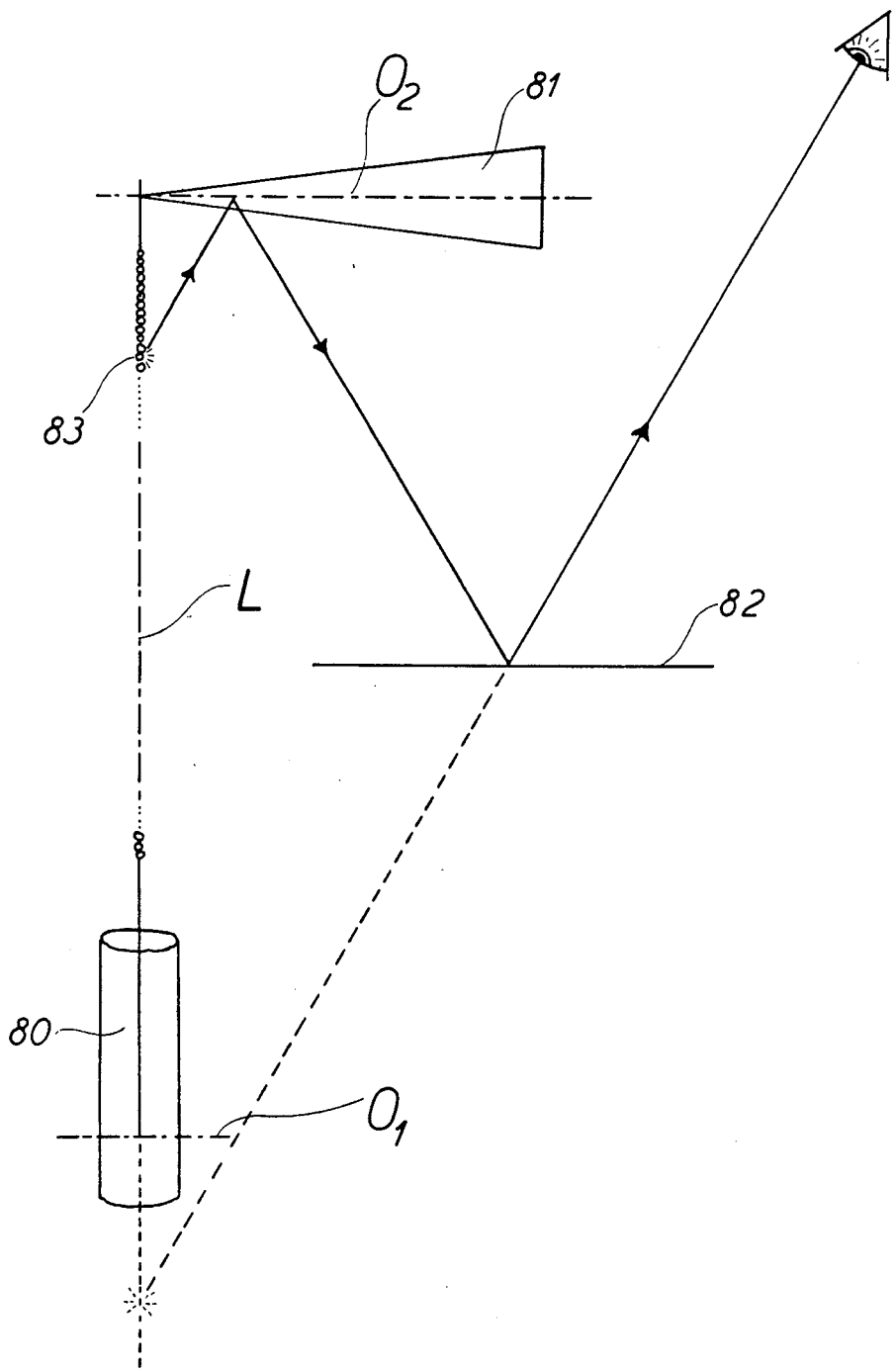
FIG. 8 shows an eigth embodiment of the invention from a side view, FIG. 9 the embodiment shown in FIG. 8, viewed schematically from the end, and FIG. 10 an arrangement of mirrors seen from in front of an apparatus.
Figure 9:
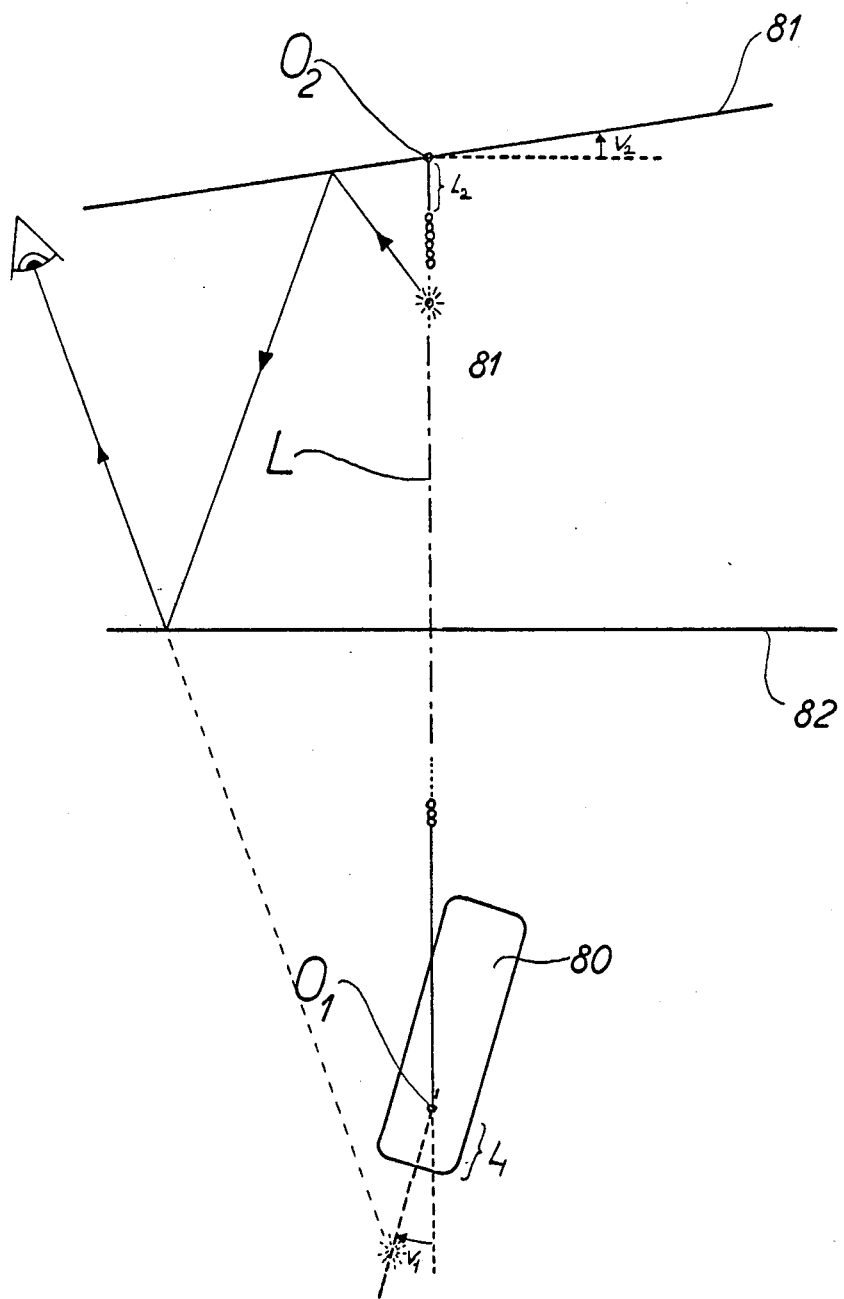

FIGS. 8 and 9 should be considered together. An ultra-sound transducer 80 is designed to tip up and down or swing forwards and backwards round an axis $O_1$, as an angle $v_1$ to the longitudinal axis L of the apparatus will then vary within the area by ±30°. A mainly triangular first mirror as shown in FIG. 8, and shown as a line in FIG. 9 is made to tip forwards and backwards round an axis $O_2$ in tact with the transducer 80, the following requirements, however, being complied with. The axis $O_2$ being parallel to the axis $O_1$, and the angle $v_2$, which the mirror 81 form to a plane perpendicular on the longitudinal axis L must at any time be half as great as the angle $v_1$. A second mirror 82 situated perpendicularly on the longitudinal axis L is situated below the first mirror 81 right in the middle between the axes $O_1$ and $O_2$. Finally, 83, indicator lamps are situated on the longitudinal axis L in a suitable manner, the following requirements being complied with. The distance $l_1$ between the axis $O_1$ and the surface of the transducer 80 is equal to the distance $l_2$ between the axis $O_2$ and the indicator lamp corresponding to the surface of the transducer. Hereafter the other parameters are adjusted to each other in such a manner that the echo-producing structure is depicted as a luminous spot in the form of an imaginary picture of the corresponding light indicator in a point, where the structure is placed. By having the mirror and the transducer swing at a frequency equal to at least 16 oscillations fields per second it will be possible by looking down into the mirror to have a standing picture of a section of the body under examination. This embodiment can likewise with advantage be applied in connection with a stationary stereo-camera, just as previously described in relation to other embodiments.

Figure 10:
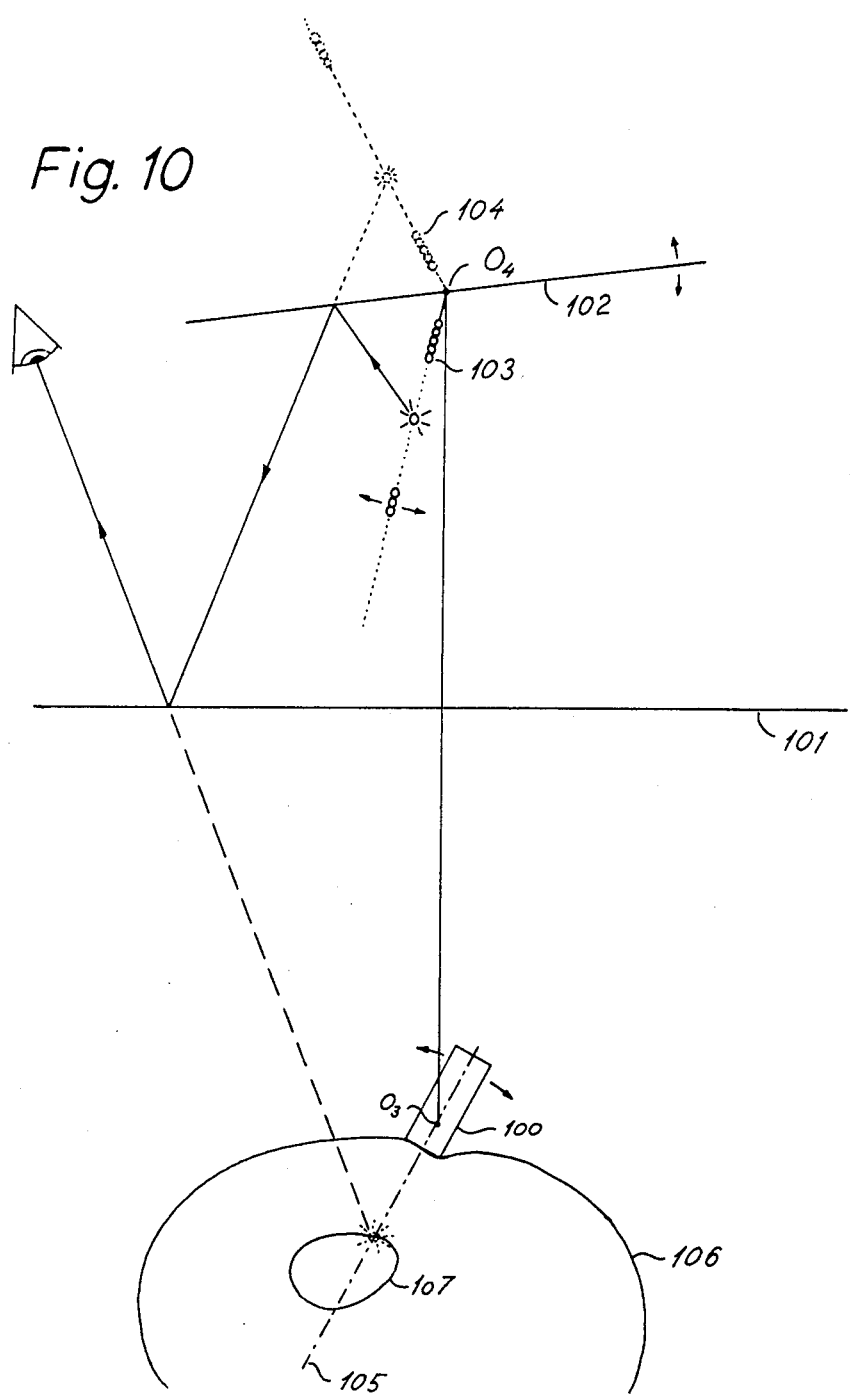

FIG. 10 shows an apparatus consisting of a swinging transducer 100 bearing against a body 106 containing an echo-producing structure 107. The first line 105, along which the impulses are emitted, is swinging with the transducer 100 round a first axis $O_3$. An indicator row 103 is designed to swing round a second axis $O_4$ running parallel to the first axis $O_3$, and in relation to the former is situated symmetrically round a first mirror 101 with an upwards turning reflecting face. A second mirror 102 with a downward-turned reflecting face is situated through the second axis $O_4$ in such a manner that a mirror image 104 of the indicator row 103 at any time will be situated so that it is symmetrical with regard to the first line 105 round the mirror 101, as it appears from the shown radiation pattern. The second mirror 102 can be stationary relative to the first mirror 101, but it may also be adjustable in relation to the latter. It should be noted, however, that an embodiment could be practicable with both a swinging indicator row and a swinging mirror, with the movements of these mechanical elements coupled together in a suitable manner. For instance could be imagined an indicator row performing a sinus shaped movement coupled together with a mirror made to swing in such a manner that the angular velocity of the reflected picture will be numerically constant.

I claim:

1. A method for facilitating the examination of an object within an optically opaque body through the use of an impulse-echo technique that includes transmitting a sequence of energy impulses into a body along a line from a source, receiving echoes from an object located within the body along said line in response to each impulse, and displaying the received echoes as luminous points on a linear array, the spacing of each luminous point from one end of the array being proportional to the distance from said source of the corresponding echo-producing point on the object, wherein the improvement comprises:

locating a reflecting surface at a reference plane between an observation point and the body such that the reflecting surface faces the observation point and intersects a line between the observation point and the object in the body;

positioning the source at a predetermined location with respect to the reference plane;

operatively coupling the linear array to the source in a predetermined relation thereto for movement, relative to the reference plane, in synchronism with movement of the source, relative to said body; and providing a reflective path from the linear array to the observation point via the reflective surface such that a virtual image of each luminous point of the array is provided by the reflective surface at an apparent location, relative to the observation point, that is coincident with the actual location of the corresponding echo-producing point on the object in the body.

2. The method of claim 1 comprising positioning the source on the side of the reference plane opposite the side having the reflecting surface.

3. The method of claim 2 comprising positioning the source at a location offset from the line between the observation point and the object in the body so that the line of transmitted impulses from the source to the object intersects the line between the observation point and the object at an angle.

4. The method of claim 1 comprising swinging the source of energy impulse transmission to scan a cross-sectional plane of the object in the body, whereby the positions of the illuminated points of the reflected virtual image of the operatively coupled linear array corresponding to each echo-producing point in the scanned plane provide an image accurately representing the cross-sectional shape of the object in said plane.

5. The method of claim 4 comprising moving the line of energy impulse transmission in a direction transverse to the plane of said swinging for scanning a multiplicity of adjacent cross-sectional planes through the object, whereby successive virtual images of the linear array projected from said reflective surface describe an accurate three-dimensional representation of the object.

6. The method of claim 1 comprising moving the line of transmitted impulses from said source to scan a cross-sectional plane of the object in the body and recording, at the observation point, the position of the illuminated points of the reflected virtual image of the operatively coupled linear array corresponding to each echo-producing point in the scanned plane, thereby providing a recorded image accurately representing the cross-sectional shape of the object in said plane.

7. The method of claim 1 comprising moving the line of transmitted impulses from said source to scan at least a portion of the volume of the object in the body and stereoptically recording, at the observation point, the position of the illuminated points of the reflected virtual image of the operatively coupled linear array corresponding to each echo-producing point in the scanned volume, thereby providing a recorded stereoptic image accurately representing the three-dimensional shape of the object in said volume.

8. Apparatus for facilitating the examination of an object within an optically opaque body, the apparatus including means for repetitively transmitting impulses of energy along a first line directed toward an object in a body and receiving echoes along the first line from the object and means for displaying said echoes as a linear array of luminous points, the points being spaced on a second line at a distance from one end of the array proportional to the distance of the corresponding echo-producing points from the transmitter, wherein the improvement comprises:
a flat mirror;
means for positioning the mirror to face a predetermined observation point and to intersect a line between the observation point and the object to be examined, the mirror defining a reference plane;
means for operatively coupling the transmitter/receiver combination to the mirror at a predetermined location relative thereto;
means for operatively coupling the linear array to the mirror at a predetermined location relative thereto; and
a reflective path between the linear array of luminous points and the observation point via said mirror for projecting a virtual image of the linear array to the observation point, such that the apparent location of each luminous point of said reflected virtual image coincides with the actual location, relative to the observation point, of the corresponding echo-producing point of the object in the body.

9. Apparatus according to claim 8 comprising:
means for periodically swinging said first line in a plane with respect to the body for scanning a predetermined sector within the body and
means for periodically swinging said linear array of luminous points synchronously with the movement of said first line so that such luminous point of the reflected virtual image, as viewed from the observation point, always coincides with the actual location of the corresponding echo-producing point in the body.

10. Apparatus according to claim 9 comprising means positioned at said observation point for recording the reflected images of said linear array of luminous points.

11. Apparatus according to claim 10 wherein said means to record reflected images comprises a liquid crystal display capable of retaining an image for at least one period of movement of said means to indicate echoes as luminous points.

12. Apparatus according to claim 10 wherein said means for recording the reflected images comprise a camera for filming three-dimensional pictures by way of stereo-technique.

13. Apparatus according to claim 10 wherein said means for recording the reflected images comprises a stationary television camera coupled together with a storage oscilloscope in such a manner that pictorial information can be summed up.

14. Apparatus according to claim 13 wherein said camera is adapted for filming of three-dimensional pictures by way of stereo-technique.

15. Apparatus according to claim 9 comprising a programmed unit to control said means for swinging said first line in order to procure an even scanning pattern.

16. Apparatus according to claim 9 wherein said means for swinging said first line and said means for synchronously swinging said linear array of luminous points provide a swinging rate sufficiently high to retain the impression of all the positions of the luminous points for one complete swing on the retina of a human eye location at the observation point; and the impulse repetition frequency is considerably higher than the swinging frequency, whereby there will be a multiplicity of impulses transmitted and sets of echoes received for each complete swing.

17. Apparatus according to claim 16 wherein:
the means for transmitting impulses and receiving echoes along a first line comprises an ultrasonic transducer mounted to pivot about a first axis spaced a predetermined distance from the reference plane on the side opposite said mirror;
an additional mirror facing the first-mentioned mirror and mounted to pivot about a second axis parallel to the first axis and spaced an equal distance from the reference plane on the same side as said first-mentioned mirror;
means for mounting said means for displaying the echoes as a linear array of luminous points to pivot about said second axis; and
means operatively coupling said display means and said additional mirror so that reflections of the luminous points in the additional mirror present a virtual image symmetrically to the corresponding echo-producing points along the first line with respect to the reference plane.

18. Apparatus according to claim 8 comprising:
means for periodically swinging said first line at a first frequency;
means to store information corresponding to the positions of the echoes;
means for periodically swinging said linear array of luminous points at a second frequency, higher than the first frequency, the second frequency being sufficiently high to retain the impression of all positions of the luminous points of the virtual images reflected to the observation point on the retina of a human eye.

19. Apparatus according to claim 8 wherein said transmitter/receiver combination and said linear array of luminous points are mounted on a longitudinally displaceable rod mounted in a fixed cardan suspension.

20. Apparatus according to claim 8 wherein:
said means for transmitting impulses and receiving echoes comprises an ultrasonic transducer, said transducer being mounted for pivotal movement about a first axis;

said means for displaying echoes as a linear array of luminous points along a second line being mounted for pivotal movement about a second axis parallel to said first axis;

the reference plane of said mirror being located equidistant between said first and second axes;

means for pivotally moving said transducer about said first axis; and means for pivotally moving said means for displaying echoes about said second axis in synchronism with the movement of said transducer.

21. Apparatus according to claim 8 wherein:

said means for transmitting impulses and receiving echoes comprises an ultrasonic transducer, said transducer being mounted to pivot about a first axis;

an additional mirror mounted to pivot about a second axis parallel to the first axis;

the apparatus having a longitudinal center line extending perpendicularly between said first and second axes, said means for displaying echoes as a linear array of luminous points being mounted coincident with said center line, the distance from said first axis to the end of the transducer being equal to the distance from the second axis to the luminous point corresponding to said end of the transducer;

means to pivotally move said transducer and said additional mirror so that the angle of rotation of said additional mirror is half the angle of rotation of said transducer;

said first-mentioned mirror being mounted in a plane equidistant from said first and second axes; and said means to display echoes as luminous points producing luminous points a distance apart on a ratio of 1:1 to the distance between the structures producing the echoes.

* * * * *

UNITED STATES PATENT OFFICE
CERTIFICATE OF CORRECTION

Patent No. 4,116,074          Dated September 26, 1978

Inventor(s) Palle Rasmus Jensen

It is certified that error appears in the above-identified patent and that said Letters Patent are hereby corrected as shown below:

Column 2, line 44, "area" should be -- are --.

Column 4, line 58, after "person 1" insert -- lying on his back --.

Column 9, line 58, "such" should be -- each --.

Signed and Sealed this

Sixth Day of February 1979

[SEAL]

Attest:

RUTH C. MASON
Attesting Officer

DONALD W. BANNER
Commissioner of Patents and Trademarks